United States Patent
Assad (10) Patent No.: US 11,622,775 B2
(45) Date of Patent: Apr. 11, 2023

(54) PULMONARY ARTERY BANDING DEVICE

(71) Applicant: Renato Sammy Assad, Sao Paulo (BR)

(72) Inventor: Renato Sammy Assad, Sao Paulo (BR)

( * ) Notice: Subject to any disclaimer, the term of this patent is extended or adjusted under 35 U.S.C. 154(b) by 728 days.

(21) Appl. No.: 16/236,410

(22) Filed: Dec. 29, 2018

(65) Prior Publication Data

US 2019/0133603 A1    May 9, 2019

Related U.S. Application Data

(63) Continuation of application No. 11/974,147, filed on Oct. 10, 2007, now abandoned, which is a continuation of application No. PCT/BR2006/000064, filed on Apr. 4, 2006.

(30) Foreign Application Priority Data

Nov. 22, 2005  (BR) .............................. PI0505102-9

(51) Int. Cl.
    *A61B 17/135*    (2006.01)
    *A61B 17/12*     (2006.01)
    *A61B 17/00*     (2006.01)

(52) U.S. Cl.
    CPC ............ *A61B 17/135* (2013.01); *A61B 17/12* (2013.01); *A61B 2017/00557* (2013.01); *A61B 2017/00809* (2013.01)

(58) Field of Classification Search
    CPC .................. A61B 17/12; A61B 17/135; A61B 2017/00557; A61B 2017/00809
    See application file for complete search history.

(56) References Cited

U.S. PATENT DOCUMENTS

| | | | |
|---|---|---|---|
| 3,538,917 A | 11/1970 | Selker | |
| 3,730,186 A | 5/1973 | Edmunds, Jr. et al. | |
| 3,831,583 A * | 8/1974 | Edmunds, Jr. .......... | A61F 2/004 128/899 |
| 3,875,928 A | 4/1975 | Angelchik | |
| 4,256,094 A | 3/1981 | Kapp et al. | |
| 4,419,985 A | 12/1983 | Trick | |
| 4,531,519 A | 7/1985 | Dunn et al. | |
| 4,543,088 A * | 9/1985 | Bootman .......... | A61M 39/0208 604/288.02 |
| 4,556,050 A | 12/1985 | Hodgson et al. | |

(Continued)

*Primary Examiner* — Jing Rui Ou
(74) *Attorney, Agent, or Firm* — Kearney, McWilliams & Davis, PLLC; William Yarbrough (57) ABSTRACT

Pulmonary artery banding device includes an inflating handing ring, to be installed around the patient's pulmonary artery, an extending tube, and an insufflating button, the extending tube connecting insufflating button to the banding inflating ring, the banding ring being configured as a C-shape hydraulic sleeve forming a support for an inflating balloon, whose external wall is formed by a thin rigid silicon layer, and whose inside wall is formed by a thin flexible silicon layer, at the apart ends of the banding ring two brims being disposed to facilitate the size banding adjustment according with the pulmonary artery caliber. The banding ring is provided with holes for passage of sutures fixating the ring on the pulmonary artery of the patient; the insufflating button being configured as a cylindrical reservoir and being provided with holes for sutures. Also a method of using the banding ring for performing a medical procedure on a patient who is an infant or neonate.

18 Claims, 9 Drawing Sheets

(56) References Cited

U.S. PATENT DOCUMENTS

| | | | |
|---|---|---|---|
| 4,673,394 A * | 6/1987 | Fenton, Jr. | ........ A61M 5/14276 |
| | | | 128/912 |
| 4,685,905 A * | 8/1987 | Jeanneret nee Aab | ...................... |
| | | | A61M 39/0208 |
| | | | 604/131 |
| 4,708,140 A | 11/1987 | Baron | |
| 5,112,303 A | 5/1992 | Pudenz et al. | |
| 5,171,253 A | 12/1992 | Klieman | |
| 5,951,512 A | 9/1999 | Dalton | |
| 6,007,516 A | 12/1999 | Burbank et al. | |
| 6,053,891 A | 4/2000 | DeCampli | |
| 6,224,619 B1 | 5/2001 | Hill | |
| 6,464,628 B1 | 10/2002 | Forsell | |
| 6,511,490 B2 | 1/2003 | Robert | |
| 7,311,717 B2 | 12/2007 | Egle | |
| 2004/0078004 A1 * | 4/2004 | Bourne | ................. A61M 39/04 |
| | | | 604/174 |
| 2004/0199129 A1 | 10/2004 | DiMatteo | |
| 2004/0254536 A1 * | 12/2004 | Conlon | ................. A61F 5/0003 |
| | | | 604/175 |
| 2005/0183730 A1 | 8/2005 | Byrum | |
| 2005/0240155 A1 | 10/2005 | Conlon | |
| 2006/0178648 A1 | 8/2006 | Barron et al. | |
| 2008/0097497 A1 | 4/2008 | Assad et al. | |

* cited by examiner

PULMONARY ARTERY BANDING DEVICE

CROSS-REFERENCE TO RELATED APPLICATIONS

This application is a continuation of U.S. patent application Ser. No. 11/974,147 filed on Oct. 10, 2007, which is a continuation of PCT International Patent Application No. PCT/BR2006/000064, filed on Apr. 4, 2006, designating the U.S. and published, in English, as PCT International Publication No. WO 2007/059594 A1 on May 31, 2007, which application claims priority to Brazilian Patent Application No. PI0505102-9 filed Nov. 22, 2005, the entire contents of each application is hereby incorporated herein by this reference.

TECHNICAL FIELD

This invention relates to improvements introduced in the Pulmonary Artery (PA) banding device that resulted in an adjustable device designed for treatment of several congenital heart lesions, such as those with excessive pulmonary blood flow, transposition of great arteries (TGA) and congenitally corrected transposition of the great arteries (CCTGA).

BACKGROUND

In general, the heart is the organ responsible for the blood circulation throughout the body. It is divided into four "compartments," namely, right atrium, left atrium, right ventricle and left ventricle.

Figure 1:
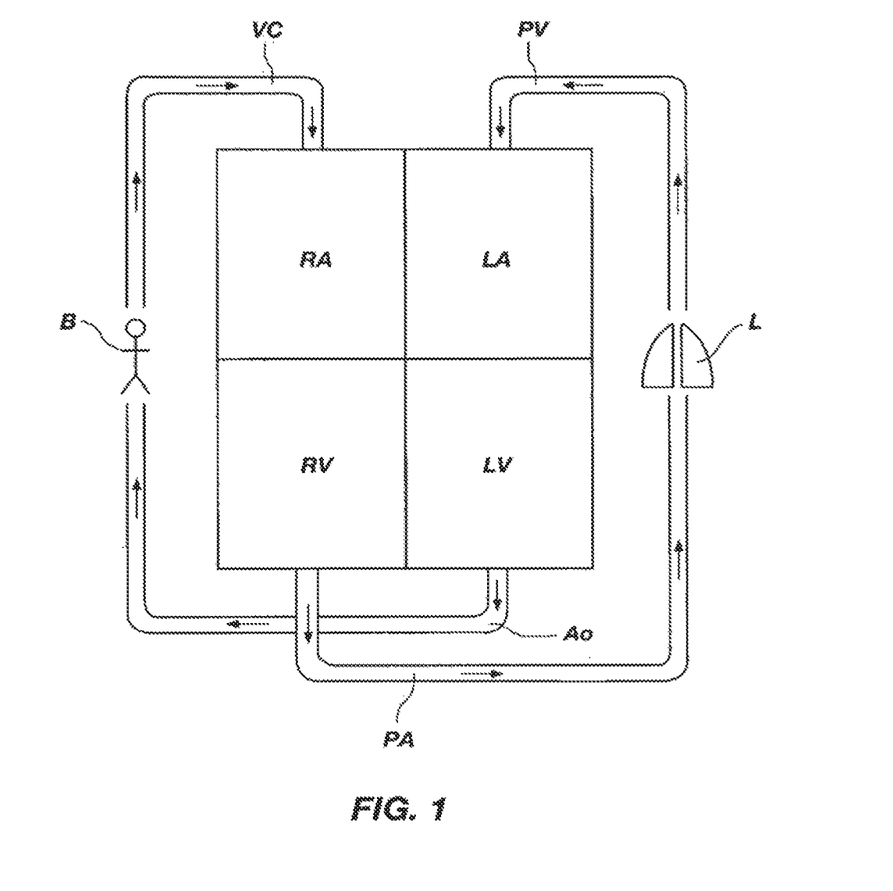
FIG. 1 shows the normal functioning of the heart.

To explain how the heart works, we describe the blood circulation through the four compartments of this organ by means of a diagram (FIG. 1): the blood comes from the body (B) to the right atrium (RA) via vena cava (VC), passes to the right ventricle (RV) through the tricuspid valve and is pumped through the pulmonary valve to the main pulmonary artery (PA). After going through the two lungs (L) where blood gases are exchanged, the now oxygenated blood returns to the heart, more specifically to the left atrium (LA), through the pulmonary veins (PV), thus completing the cycle known as "small circulation." Now, blood goes through the mitral valve to the left ventricle (LV), from where it is ejected through the aortic valve to the aorta (Ao), and from there throughout the body. The "great circulation" circuit is now completed by the venous blood return to the right atrium.

Therefore, the right ventricle is responsible for pumping blood to the lungs for gas exchange, while the left ventricle is in charge of pumping oxygenated blood to the whole body. For this reason, it is named as the systemic ventricle, much more overloaded than the right ventricle.

Some congenital heart lesions are associated with excessive pulmonary blood flow, in some special circumstances requiring palliative treatment to somehow diminish this excessive pulmonary blood flow until subsequent definitive treatment is possible.

Among the lesions commonly producing heart failure beyond age one to two weeks when diminished pulmonary vascular resistance allows substantial left-to-right shunting, is the multiple ventricular septal defect, more specifically between the right and left ventricles. In these cases, the right ventricle, besides receiving blood from the right atrium, also receives blood from the left ventricle through these multiple orifices, promoting excessive pulmonary blood flow. Babies born with this anomaly usually have feeding difficulties and failure to gain weight and grow.

However, some small infants may be very sick, making it difficult to completely repair the lesion. This is one example of congenital heart malformation whose palliative treatment aims to limit excessive pulmonary blood flow. Surgical treatment can be well managed initially by PA banding to limit the excessive blood flow to the lungs, resulting in deferred repair until the patient can be submitted to definitive surgery.

The PA banding technique continues as a valuable therapeutic intervention for complex defects even during the era of total correction of congenital cardiac anomalies during the neonatal period. It consists of placing a band well proximal to the pulmonary artery bifurcation. The band is tightened and secured by suture to narrow the main pulmonary artery, bringing about a balance of pulmonary and aortic blood flow by equalizing outflow resistance. Excessive blood flow to the lungs is therefore diminished by constricting the circumference of the pulmonary artery, thereby achieving the desired limitation of the pulmonary flow.

However, adjustment of the required degree of pulmonary and aortic blood flow is the most difficult aspect of the procedure. We rely on pressure measurements in the aorta and PA distal to the band. The main PA is narrowed until the pressure distal to the band is one-third to one-half that of the aorta. Nevertheless, skill and accuracy of the surgery, supplemented by good fortune, are most likely to assure success in this imprecise procedure.

In addition, the band commonly used is fixed and unchanged in the postoperative course. In other words, it does not allow for postoperative adjustability, that is, it is not possible to control precisely and accurately the cross-sectional diameter of the pulmonary artery according to the patient's clinical condition. It means that the adjustment of the traditional band is unpredictable and empiric, performed under artificial conditions, different from the postoperative period.

There are also other congenital heart lesions that may benefit from an adjustable PA banding system. One example is the Transposition of the Great Arteries (TGA). For a better understanding of this congenital malformation, FIG. 2 schematically describes this condition:

TGA is a condition in which the atria and the ventricles are concordant, while the ventricular-arterial relationship is discordant. Therefore, the aorta (Ao) arises anteriorly from the right ventricle (RV), while the pulmonary artery (PA) arises posteriorly from the left ventricle (LV), i.e., babies born with this malformation have the great arteries, PA and Ao, inverted. The anatomical arrangement results in two separate and parallel circulations: firstly, oxygenated blood coming from the lungs returns successively to the lungs without being delivered throughout the body; secondly, blood goes to and returns from the body totally unoxygenated (since it does not exchange gases through the lungs).

Figure 2:
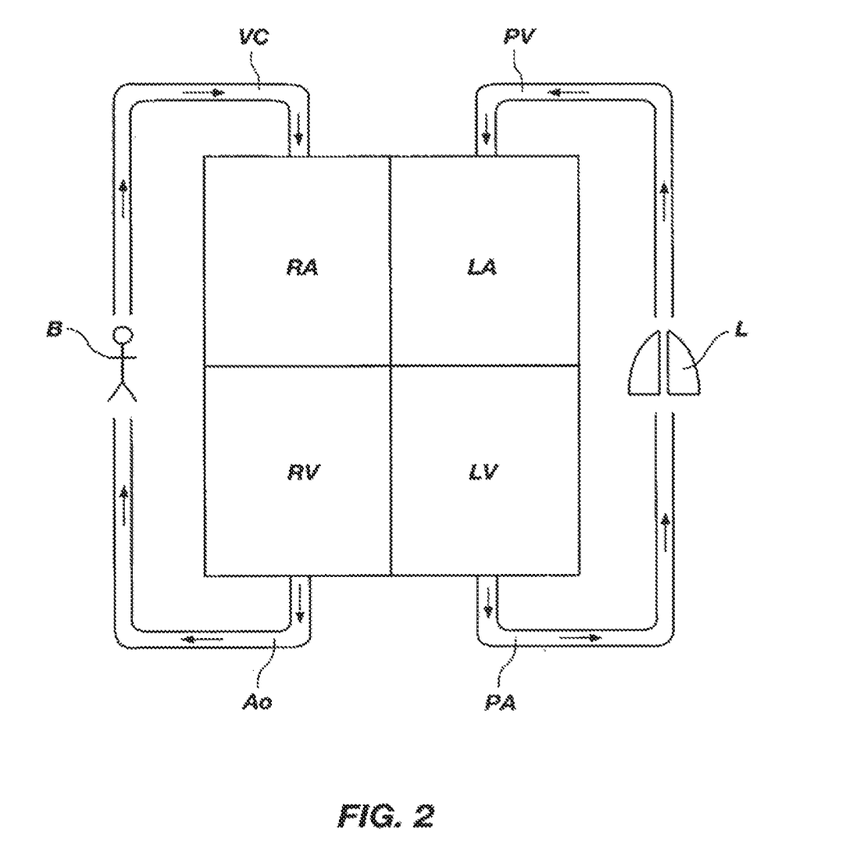
FIG. 2 shows the schematic diagram of Transposition of the Great Arteries (TGA)

Thus, as shown in FIG. 2, unoxygenated systemic venous blood returns from the body (B) to the right atrium (RA) via vena cava (VC), as usual. The bloodstream goes on to the RV through the tricuspid valve, but instead of being pumped to the main PA, it is directed inappropriately to the Ao and systemic circulation. On the other hand, oxygenated pulmonary venous blood coming from the lungs via the pulmonary veins (PV) is directed to the LA and then to the LV, to be ejected back to the pulmonary circulation, where it is re-oxygenated.

A baby born with this anomaly presents with inadequate gas exchange and suffers from cyanosis. Life is sustained exclusively through connections between the two circuits. If not treated, more than 50% of patients die during the first months of life, unless there is communication between these two circulations.

Basically, there are two options for TGA repair: redirection of venous inflow or redirection of ventricular outflow. The first one redirects pulmonary venous return toward the tricuspid valve and systemic venous return toward the mitral valve, known as atrial switch operation or Senning operation.

Secondly, the operation consists of switching the great arteries, a technique introduced by Jatene in 1975, also known as arterial switch operation. In this technique, the aorta is surgically connected to the LV and the main PA to the RV. It is now recognized that the Jatene operation can be done only with a LV conditioned to pump against systemic resistance. Therefore, the procedure must be performed during the neonatal period, due to the following reasons:

1. When the baby with TGA is still in the mother's womb, the two ventricles work together (in parallel), because of two communications between the compartments of the heart: the foramen ovale at the atrial level and the ductus arteriosus at the arterial level (communication between the great arteries). This has an important physiological implication since the two ventricles present with the same muscular mass.

2. Accordingly, when the baby is born, the postnatal LV ejects blood into the low-resistance pulmonary vasculature and, therefore, does not increase its muscle mass relative to the right (systemic) ventricle (or relative to a normal left ventricle). Consequently, within weeks, the LV myocardium loses its capacity to maintain an adequate cardiac output, against a systemic afterload. Therefore, LV muscle growth is retarded because the afterload (pulmonary resistance) is low. Instead, the RV assumes the function, and also the necessary muscle mass, to overcome systemic resistance. These significant differences in LV and RV muscle mass progress over time and may assume considerable importance if the LV is suddenly required to perform against systemic resistance, as in the arterial switch operation.

It is important to take advantage of these anatomic features during the neonatal period, in which both ventricles present the same muscle mass, to carry out the Jatene operation, when the LV is still adequate to handle systemic circulation.

3. In case of late referral (beyond the neonatal period), the primary Jatene Operation will no longer be possible. There is increasing likelihood that the LV will be unable to accommodate the increased workload. The LV, connected to the low pulmonary vascular resistance, becomes more and more hypotrofic, while the RV, connected to the high systemic vascular resistance, becomes more and more hypertrofic.

A number of circumstances can arise that cause postponement of surgery beyond the "safe" period for an arterial switch operation. For example, a neonate may be seriously ill with necrotizing enterocolitis, renal or hepatic failure, or a hemorrhage in the central nervous system. Also, the neonate may be geographically distant from a center offering the arterial switch operation.

Because of these possibilities, the arterial switch operation must be performed after preliminary pulmonary artery banding, with or without a systemic to pulmonary artery shunt, to stimulate the development of LV muscle mass, followed by an arterial switch operation some months later, a concept introduced by Yacoub et al. in 1977. In the first stage, the LV must be stimulated by systolic overload of PA banding to retrain the ventricle and promote muscle mass acquisition. The retraining period between the two stages will allow the LV to function as a systemic pump. In the second stage, once the ideal LV mass acquisition has been achieved to support systemic circulation, the Jatene operation can be performed.

With the advance of molecular biology in the 80's, laboratory studies in rats have demonstrated surprisingly rapid induction (within 48 hours) of the genes responsible for the isozyme adaptation of the myocardial myosin, actin, and tropomyosin in response to an acute pressure load. It has been demonstrated that the process of cardiac hypertrophy is associated with changes in the genetic expression of the cardiomyocytes and fetal contractile proteins when a systolic load is applied to the ventricle. In fact, cardiomyocyte systolic load can trigger a genetic response that increases the protein synthesis, the beginning of hypertrophic process.

Some years later, the Boston Children's Hospital introduced the concept of rapid, two-stage arterial switch operation for TGA, limiting the interval between the first and the second operation town average of seven days. However, the good results obtained by the Boston Group were not reproduced in other centers, where high morbidity and mortality rates were present. That is why application of the two-stage arterial switch operation to this subset of patients became of interest to many investigators. Several studies have been carried out to achieve the most physiological way to obtain this LV retraining, with no impairment of late LV function.

Nevertheless, some inconvenient aspects of PA banding deserve to be mentioned:

Traditional PA banding with a fixed tape stir up a great deal of surgical skill and ability to be placed properly during surgery, proximal enough to avoid distortion of the PA branches. Fine adjustment of such banding is hard to achieve.

The difficulty in achieving an appropriate tightness of the band can be readily explained when it is recalled that Poiseuille's law predicts that blood flow is related to the fourth power of the radius of the vessel. Therefore, a minor alteration in diameter will have a large impact on flow and pressure gradient across the band site.

Banding adjustment is made in an anesthetized, mechanically ventilated patient with an open chest, and the physiology is clearly quite different from that in an awake and spontaneously breathing child.

There is yet another possibility of clinical application of adjustable PA banding device, called "Congenitally Corrected Transposition of the Great Arteries" (CCTGA), in which there are both atrioventricular and ventriculoarterial discordant connections. For a better understanding of this condition, FIG. 3 describes such connections.

Figure 3:
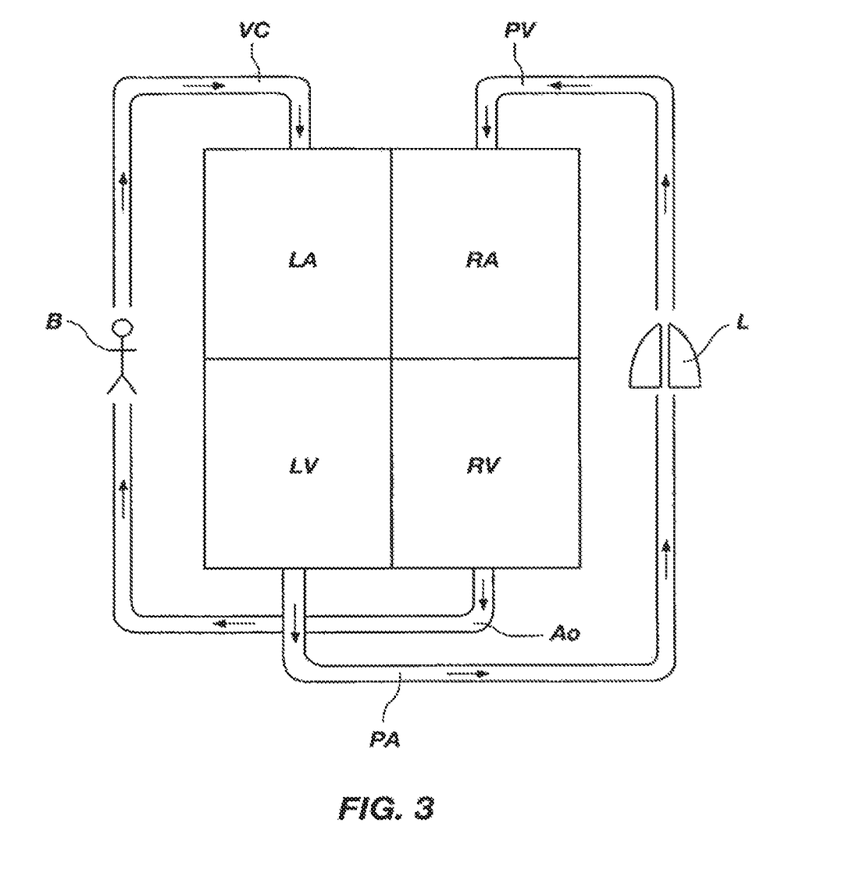
FIG. 3 shows the schematic diagram of Congenitally Corrected Transposition of the Great Arteries (CCTGA)

Babies born with this condition present correct blood circulations, but morphologically speaking, their right and left ventricles are inverted. Unoxygenated blood coming from the body (B) via vena cava (VC), reaches the right atrium (RA), which connects through a morphologic mitral valve with a rightward and anteriorly positioned morphologic left ventricle. This finely trabeculated ventricle connects with an outflow tract and then with a somewhat posteriorly positioned pulmonary artery. Bloodstream follows to the lungs (L) where gases are exchanged. Oxygenated blood returns to the heart via pulmonary veins (PV). The left atrium connects through the tricuspid valve with a coarsely trabeculated right ventricle (RV). The right ventricular outflow tract is located anteriorly and leads to a leftward-positioned aortic valve and ascending aorta. RV then ejects oxygenated blood to the whole body circulation. Therefore, this arrangement allows for a normal circulation in the absence of other defects.

Although the survival of patients with CCTGA is dictated largely by the associated defects, life expectancy is diminished for patients even with the isolated form of the condition. A number of studies have confirmed that life expectancy is substantially diminished even for patients who have reached adulthood. The most common cause of death is congestive heart failure secondary to morphologically right (systemic) ventricular dysfunction, often associated with regurgitation of the tricuspid valve. The traditional surgical approach to the treatment of patients with CCTGA maintains the morphologically RV and tricuspid valve in the systemic circulation. However, dysfunction of the systemic (morphologically right) ventricle or systemic atrioventricular (tricuspid) valve tends to develop and worsen with time, which may lead to significant morbidity and mortality. Tricuspid regurgitation has been addressed by replacement of the systemic atrioventricular valve. Nevertheless, this procedure is often unsuccessful in preventing or reversing right ventricular dysfunction.

There are indeed anatomical and physiological considerations that support the assumption that the left ventricle is more suitable than the right to serve the systemic circulation. First of all, the left ventricle (with its cylindric shape, its concentric contraction pattern, and both the inlet and outlet orifices situated in close proximity) seems ideally adapted to work as a pressure pump, whereas the right ventricle (with its crescent-shaped cavity, its large internal surface area-to-volume ratio, its bellows-like contraction pattern, and its more separated inlet and outlet segments) seems better suited to serve as a low-pressure volume pump chamber. Also, the left ventricle has two coronary arteries (left anterior descending and circumflex), while the right ventricle has only one (right coronary).

Furthermore, the papillary muscles of the RV are small and numerous, originating both from the septum and from the right ventricular free wall, in contrast to the two papillary muscles of the LV. This architecture allows the tricuspid valve to be pulled apart as the right ventricle dilates, leading to tricuspid regurgitation. In long-term, patients with CCTGA begins to dilated RV and the tricuspid annulus (which is the systemic valve), allowing RV blood regurgitation during ventricular contraction and, consequently, pulmonary congestion and dyspnea.

The high rate mortality associated with the traditional approach has stimulated a number of groups to propose a more anatomic repair on the basis of the hypothesis that establishment of atrioventricular and ventriculoarterial concordance would improve the long-term survival of patients with this anomaly. This approach has been named as the double switch operation, i.e., atrial level circulation switch by the Senning procedure and arterial switch operation by the Jatene procedure at the same time. Such approach has the appealing theoretic advantage of placing the morphologically LV and mitral valve in the systemic circulation, thus relieving the hemodynamic burden on the RV and tricuspid valve.

Many of these patients are older and are seen because of right ventricular failure, usually with tricuspid valve regurgitation and often without associated defects. As would be expected in these cases, the LV is physiologically unprepared to sustain systemic pressure and resistance because it has been working as the pulmonary ventricle. Therefore, double switch procedure must be performed after a preliminary PA banding procedure to recondition the LV. Because of the high degree of variability among these patients, optimal band tightness is not always achieved on the first effort and is often limited by the onset of LV dysfunction.

The retraining process of the LV, especially in older patients, may take months before obtaining the necessary LV hypertrophy to sustain systemic pressure and vascular resistance. In addition, as has been described in the literature, there is the need for subsequent reoperations to readjust PA banding in cases where a patient cannot achieve adequate LV hypertrophy.

In the light of what has been described above, it sounds like traditional PA banding used to treat the above-mentioned heart lesions (those with pulmonary congestion, TGA and CCTGA), is inconvenient in that it does not allow late and fine adjustment according to the patient's clinical condition. In addition, it does not afford precise and accurate alteration in PA diameter over time and, therefore, always requires new interventions to achieve that.

To deal with those problems, some researchers have endeavored to create a banding device that allows postoperative PA diameter fine adjustment with no need for reinterventions, the so-called "adjustable PA banding devices."

Some of the historical aspects conceptually related to our prototype are described here. The idea of adjustable banding devices composed of a hydraulic cuff and a self-sealing button was first proposed in 1957. In fact, Jacobson and McAllister proposed a device that consisted of a rubber cuff with a lateral opening and connected to a reservoir protected by self-sealing rubber. It was used on the great vessels of dogs, aiming a congestive heart failure model. Complications in handling the device were observed. In 1969, Bishop and Cole improved the Jacobson and McAllister device by covering the cuff with silicone, with the aim of reducing local tissue reaction. They induced RV hypertrophy and congestive heart failure in a dog model. In 1972, Edmunds and associates introduced two main changes: an external, nondeformable layer on the hydraulic cuff and silicone, instead of rubber. However, they observed asymmetric inflation or rupture of the cuff, and leakage of the injected material prevented it from clinical use. In 1985, a new device made of biologically stable material (medical grade silicone) was introduced by Park et al. The cuff was covered with reinforced braid and coated with silicone. The self-sealing button has a silicone diaphragm which did enable repeated needle puncture, avoiding leaking through the button. The device implanted in dogs and lambs was easily and effectively adjusted. In that same year, Solis et at proposed a similar device to the previous one, intended to prepare the subpulmonary ventricle for the two-stage Jatene operation for the first time in the literature. Nevertheless, when the system was submitted to a high gradient pressure, as in the systemic circulation, dilation of the reservoir and the connecting tube occurred. In addition, there was a tendency of the cuff to bulge laterally under high pressure. In another study, the same group improved the strength of the material by reinforcing the cuff and the connecting tube with a spiral of 4-0 silk to withstand systemic arterial pressure. Again, they experienced bulging of the cuff due to a loosing silk.

Given the numerous problems encountered in all of these studies described above, at the present, an adjustable PA banding device that could be safely applied to humans and afford fine PA diameter adjustments is not available yet.

SUMMARY OF THE INVENTION

This patent refers precisely to improvements introduced in our PA banding device, published in the *Journal of*

*Thoracic and Cardiovascular Surgery,* volume 124, pages 999 through 1006, in the year of 2002. Our prototype was made of three parts: banding ring, extension tube, and inflation button. The banding ring was a U-shaped hydraulic cuff, with 10 mm internal diameter and 5 mm width. Its outer layer consisted of 1 mm thick rigid silicone, which kept it from deforming. The inner surface had a deformable layer of silicone, which expanded, compressing the lumen of the vessel, according to the volume injected into the inflation button. At the two ends of the cuff, there were small orifices that were used for securing the ring to the PT. The extension tube, also made of silicone, linked the banding ring with the inflation button. It had a 2 mm inner diameter and was 25 cm long. The inflation button was a separate circular reservoir made of self-sealing silicone, in which base included a metal plate. The reservoir had a port, which was connected to the extension tube. This button was implanted subcutaneously, thus permitting the inflation or deflation of the banding ring percutaneously. However, the connection between the inflation button and the extension tube used began to leak over time due to the developed high internal pressure and to the fact that is was not hermetically sealed.

Improvements of the PA banding device proposed here resulted in an adjustable and more delicate banding system, completely hermetic, and percutaneously adjustable, to be used in the congenital heart lesions described above.

With improvements, the device is now comprised of the following components:

1. A banding ring C-shaped hydraulic cuff with a thinner outer layer, less than 0.5 mm thickness silicone, reinforced with a Dacron mesh, that keeps it from deforming centrifugally;

2. An inflation button to be implanted subcutaneously in the patient's thorax, connected hermetically to each other (sealed during manufacturing) with a thinner extension tube (inner diameter less than 1.5 mm). The extension tube takes the liquid injected percutaneously in the inflation button to the banding ring, thus varying the PA diameter according to the amount of injected liquid.

The inner wall of the banding ring is formed by a very thin and flexible silicone that allows centripetal distension. The applied material in the banding ring is potentially able to increase 500% in volume size, promoting a wide range of reversible constriction of the banded blood vessel.

Therefore, our new PA banding device prototype differs from earlier experimental models in that it presents a Dacron mesh that reinforces the outer layer and makes it thinner, keeping it from centrifugal distension when inflated.

In addition, the outer layer prolongs besides the silicone cuff at the distal ends of the banding ring, making it possible to choose the appropriate diameter of the banding ring according to the vessel diameter. These outer layer prolongations can be sutured to fix the diameter of the band. The Dacron mesh reduces the likelihood that the sutures will cut through the banding material.

The outer layer of the banding ring also presents some small side straps to attach the banding ring to the PA adventitia with sutures to keep it from migrating distally and impinging on the PA bifurcation.

The inflation button is configured by a cylindrical reservoir made of a thick self-sealing silicone whose base has a plate (preferably made of porcelain) to limit the needle introduction for liquid injection. The button comes with multiple side holes around its base to fix it with sutures in the subcutaneous tissue.

Once the adjustable banding ring has been placed in the patient's PA and the inflation button placed subcutaneously in the chest wall, the banding ring constriction can be adjusted after full recovery from anesthesia. It will be possible to control precisely and accurately the cross-sectional diameter of the PA in the postoperative period, according to the patient's clinical condition. It means that PA banding adjustment will be predictable and performed under chronic conditions in an ambulatory patient. By injecting or removing liquid percutaneously from the inflation button, the banding ring is inflated or deflated, thereby determining the desired flow and pressure in the distal pulmonary artery, according to the specific congenital heart lesion being treated.

All of the reasons mentioned above ensure that improvements established in this PA banding system can offer a biocompatible device that is easy to implant and efficient for reversible and adjustable percutaneous PA banding. It can be used in situations to control excessive pulmonary blood flow, as well as for LV retraining. The device may, therefore, be used in the treatment of several congenital malformations.

The improved PA banding device permits a percutaneous control of PA diameter and a perfectly precise regulation of pulmonary blood flow and pressure, producing a fine and reversible adjustment that has not been achieved by previous banding devices.

This invention refers to improvements introduced in the adjustable banding system, comprised of a mini inflatable banding ring (4 mm diameter) to be placed around the patient's pulmonary artery, and an inflation reservoir to be implanted subcutaneously in the patient's chest wall, connected hermetically to each other from industry by means of connecting tubing. Its dimensions were planned for use in low birth neonates, considered as high-risk patients for more traditional approaches. All parts of the Adjustable Banding System are made of biologically stable material (medical grade silicone) and produced with radiopaque material to be visualized on chest roentgenogram, in order to provide information regarding the position of the implanted device.

The device is comprised of a banding ring C-shaped hydraulic cuff. The inner wall of the banding ring is formed by a very thin and flexible silicone that allows centripetal distension, and covered with a thin layer (0.5 mm thick) of silicone reinforced with a polyester mesh. The banding ring balloon is potentially able of 500% increase in volume size, promoting a wide range of reversible constriction of the banded blood vessel. When the cuff is uninflated, the measured diameter can be as low as 4 mm. There are two apart ends of the hydraulic cuff, a prolongation of the non-distensible outer wall, planned for further fine adjustment of the hydraulic cuff, when placed around the artery, by suturing together the ends. The outer layer of the banding ring presents some small flanges along the non-apart borders, which are used for securing it firmly with sutures to the adventitia of the artery. This keeps the adjustable banding system from migrating distally and impinging on the pulmonary artery bifurcation. The connecting tubing has 0.9 mm inner diameter.

The inflation reservoir used to pump fluid to the hydraulic cuff consists of a ceramic cylindrical reservoir, with a self-sealing silicone diaphragm at the top, which keeps the banding system leak proof after repeated needle punctures of the reservoir. The reservoir has four small holes around the rim to enable suturing to subcutaneous tissue. It allows percutaneous adjustment of the pulmonary artery banding cuff volume as many times as needed, with no need for further surgical interventions.

The invention may further be viewed as the improvements in an ADJUSTABLE BANDING SYSTEM, adapted to restrict blood flow through the small pulmonary arteries of neonates, comprises an inflating banding ring, to be implanted around the neonate PA branches, a connecting tubing and a self-sealing inflating reservoir, implanted in the patient's subcutaneous thorax. All parts of the Banding System are made of or covered by medical grade silicone and are produced with radiopaque material to be visualized on chest roentgenogram, in order to provide information regarding the position of the implanted device.

The banding ring is configured as a "C" shape hydraulic cuff, with an outer wall formed by a thin non-distensible silicone layer, or similar, that prevents centrifugal distention of the hydraulic cuff. Some small flanges may also be present to attach the banding ring to the PA adventitia with sutures to keep said banding ring from migrating distally. The inner portion of said banding ring is formed by a thin flexible and distensible silicone balloon, or similar, that allows inward distension as it is inflated.

The "C" shaped banding ring ends in two apart ends for adequate sizing of the band according to neonate's PA size. The twist-resistant and non-distensible flexible connecting tube provides the communication between the banding ring and the inflating reservoir, with the purpose of taking the fluid injected percutaneously in the inflation reservoir to the banding ring, thus varying the PA diameter according to the volume of injected fluid.

The inflating reservoir is configured by a ceramic cylindrical sink, with a self-sealing silicone diaphragm at the top and a lateral aperture connected hermetically to the tube. A 3 mm thick silicone base has four small holes around the rim to enable suturing to subcutaneous tissue. The banding ring constriction can be adjusted by injecting or removing fluid percutaneously from the inflation reservoir.

In a further embodiment the instant invention is directed to improvements introduced in the adjustable banding system, comprised of a mini inflatable banding ring (4 mm diameter) to be placed around the patient's pulmonary artery, and an inflation reservoir to be implanted subcutaneously in the patient's chest wall, connected hermetically to each other from industry by means of connecting tubing. Its dimensions were planned for use in low birth neonates, considered as high-risk patients for more traditional approaches.

All parts of the Adjustable Banding System are made of biologically stable material (medical grade silicone) and produced with radiopaque material to be visualized on chest roentgenogram, in order to provide information regarding the position of the implanted device.

The device is comprised of a banding ring C-shaped hydraulic cuff. The inner wall of the banding ring is formed by a very thin and flexible silicone that allows centripetal distension, and covered with a thin layer (0.5 mm thick) of silicone reinforced with a polyester mesh. The banding ring balloon is potentially able of 500% increase in volume size, promoting a wide range of reversible constriction of the banded blood vessel. When the cuff is uninflated, the measured diameter can be as low as 4 mm. There are two apart ends of the hydraulic cuff, a prolongation of the non-distensible outer wall, planned for further tine adjustment of the hydraulic cuff, when placed around the artery, by suturing together the ends.

The outer layer of the banding ring presents some small flanges along the non apart border, which are used for securing it firmly with sutures to the adventitia of the artery. This keeps the Adjustable Banding System from migrating distally and impinging on the pulmonary artery bifurcation. The connecting tubing has 0.9 mm inner diameter.

The inflation reservoir used to pump fluid to the hydraulic cuff consists of a ceramic cylindrical reservoir, with a self-sealing silicone diaphragm at the top, which keeps the banding system leak proof after repeated needle puncture of the reservoir. The reservoir has four small holes around the rim to enable suturing to subcutaneous tissue. It allows percutaneous adjustment of the pulmonary artery banding cuff volume as many times as needed, with no need for further surgical interventions.

BRIEF DESCRIPTION OF THE DRAWINGS

For didactic purposes, diagrams of this device are listed below.

DETAILED DESCRIPTION OF THE INVENTION

The object of the present patent of invention refers to improvements introduced in the pulmonary artery banding device, the device (1) thus constituted by a banding inflating ring (2) to be installed around the patient's pulmonary artery (PA) by an extending tube (3), and by an insufflating button (4), implanted subcutaneary in the patient's thorax, being the extending tube (3) connecting the insufflating button (4) to the banding inflating ring (2), keeping everybody linked to each other.

Figure 4:
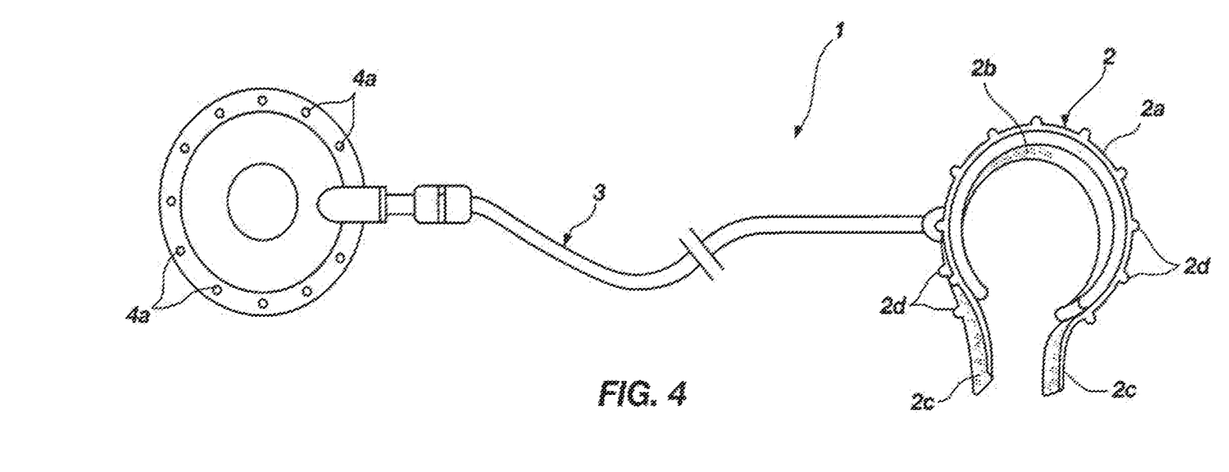
FIGS. 4 and 5 illustrate the PA banding device from the top and in a lateral view.
Figure 5:
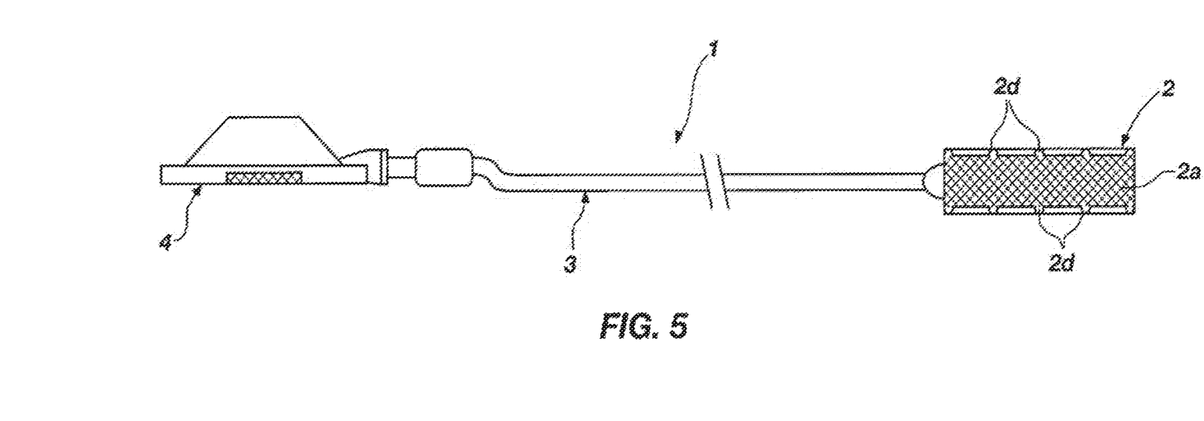

According to the present improvements and as showed in FIGS. 4 and 5, the banding ring (2) is configured by a hydraulic sleeve in the shape of "C," forming a support for an inflating balloon, whose external wall (2a) is formed by a thin rigid silicon layer, composed by a Dacron mesh, that prevent the radial distention of the ring from within inside to outside (centrifugal distention), and whose inside wall (2b) is formed by a thin flexible silicon layer that allows the outside radial distention of the ring from within outside to inside (centripetal distention).

This way, the banding ring (2) of the device is now improved and differs from the previous experimental models by being thinner and presenting a reinforcement through a screen in the sleeve outside wall that prevents the centrifugal distention, when insufflating. Thus, the banding ring (2) has the property of not centrifugal stretching out, but has the plenty centripetal stretching out, could increase of volume, meaning, until up to 500% from the initial volume.

At the apart ends of the banding ring (2), two brims are foreseen (2c) that facilitate the size banding adjustment according to the pulmonary artery caliber (PA), through fastening and fixation passage points (sutures) between the same ones.

The banding ring (2) is still provided of an appropriate number of holes or loops with holes (2d), along all extensions of its non apart borders, placed equidistant spaced to each other, for fixation points (sutures) passage of the ring in the patient's pulmonary artery to avoid the banding ring migration (displacement) to the pulmonary artery, along the blood flow that goes by the interior of the body.

The extending tube (3), also of silicon, provides the communication between the banding ring (2) and the insufflating button (4), with the purpose of transmitting an appropriate liquid injected into the button for the banding ring sleeve.

The insufflating button (4) is configured by a cylindrical reservoir made in auto-stamped silicon, whose base presents a porcelain metallic plate to limit the introduction injection liquid needle point; the button (4) is provided with a multiplicity of holes (4a) disposed close to the outlying border, to passed the fixation points (sutures) of the button (4) in the patient's body, more specifically, in the patient subcutaneous (under the skin), allowing the banding ring (2) insufflation or "unsufflation" by percutaneous path.

Figure 6:
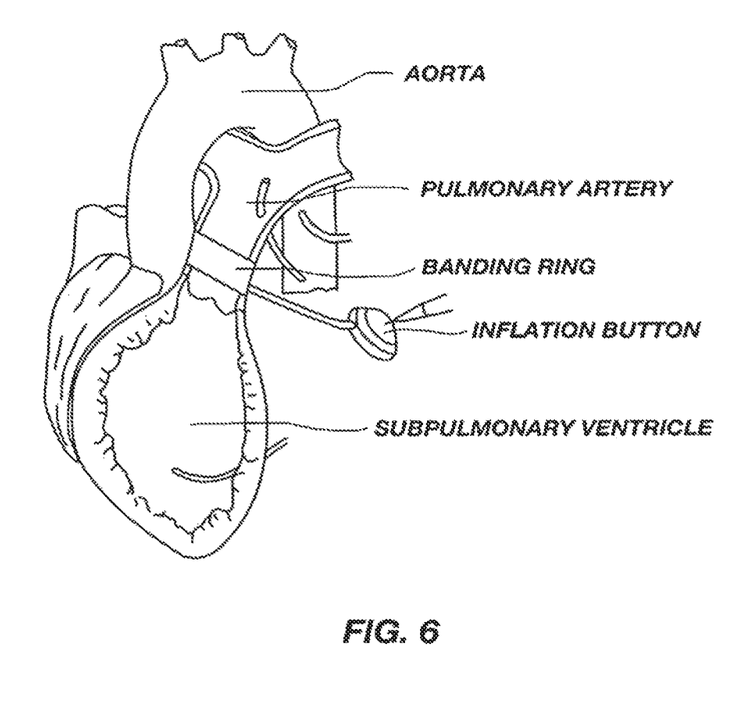
FIG. 6 is a schematic illustration of PA banding implantation.
Figure 7:
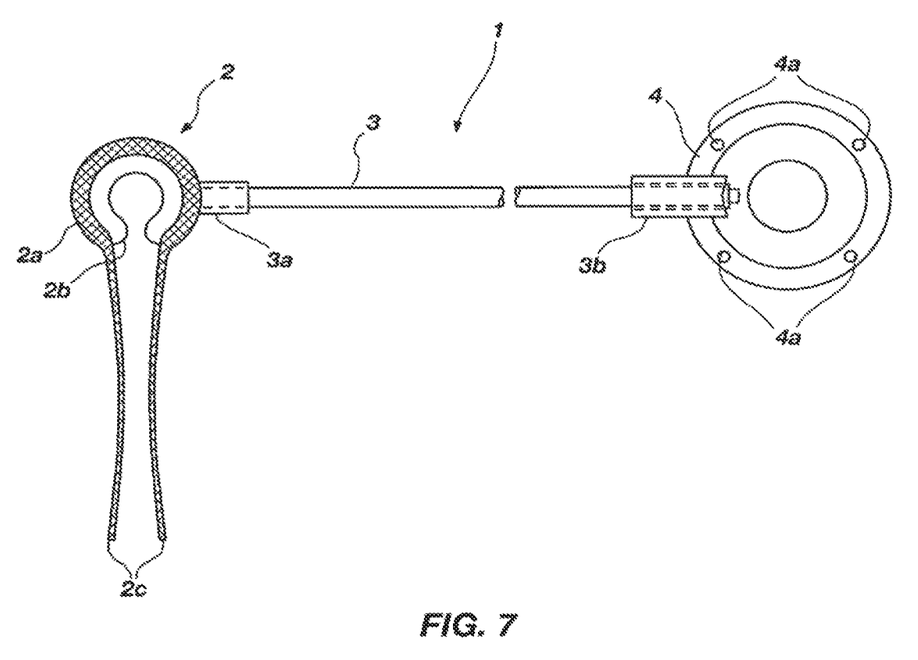
FIG. 7 is a front elevational view of an alternative embodiment of the mini adjustable banding system of the instant invention.
Figure 8:
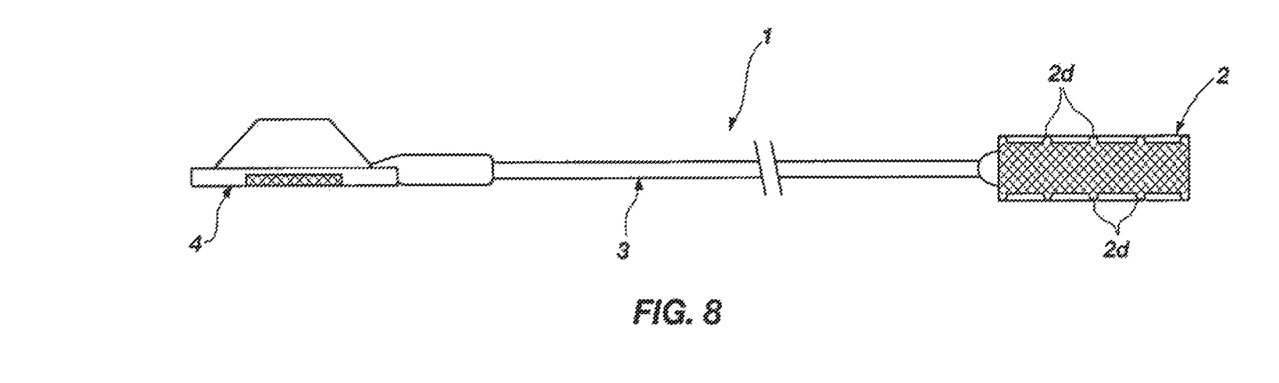
FIG. 8 is a side elevational view of the mini adjustable banding system of FIG. 7.
Figure 9:
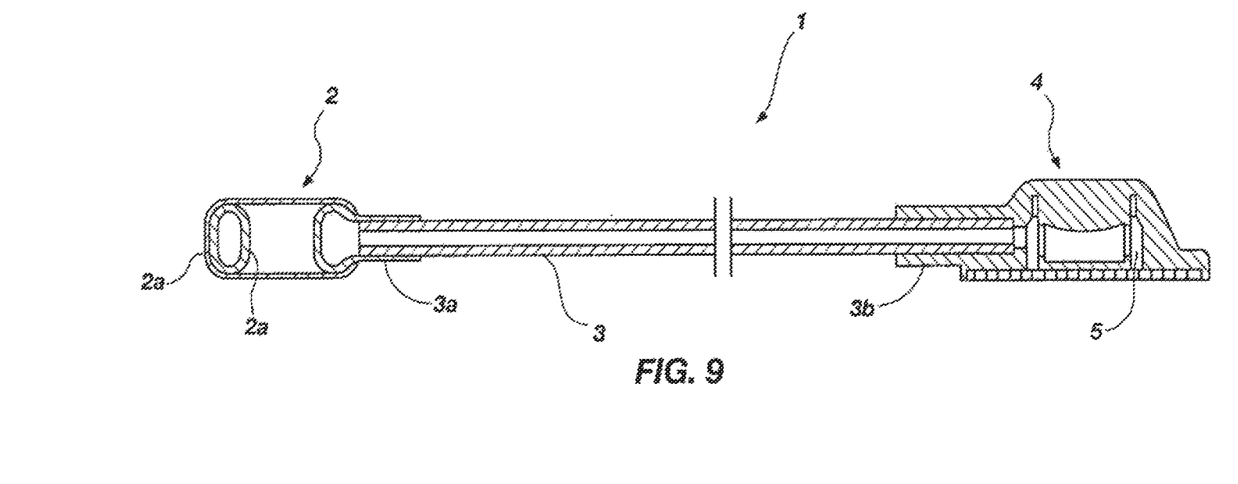
FIG. 9 is a cross sectional view of the mini adjustable banding system of FIG. 7 taken along section lines Q-Q.
Figure 10:
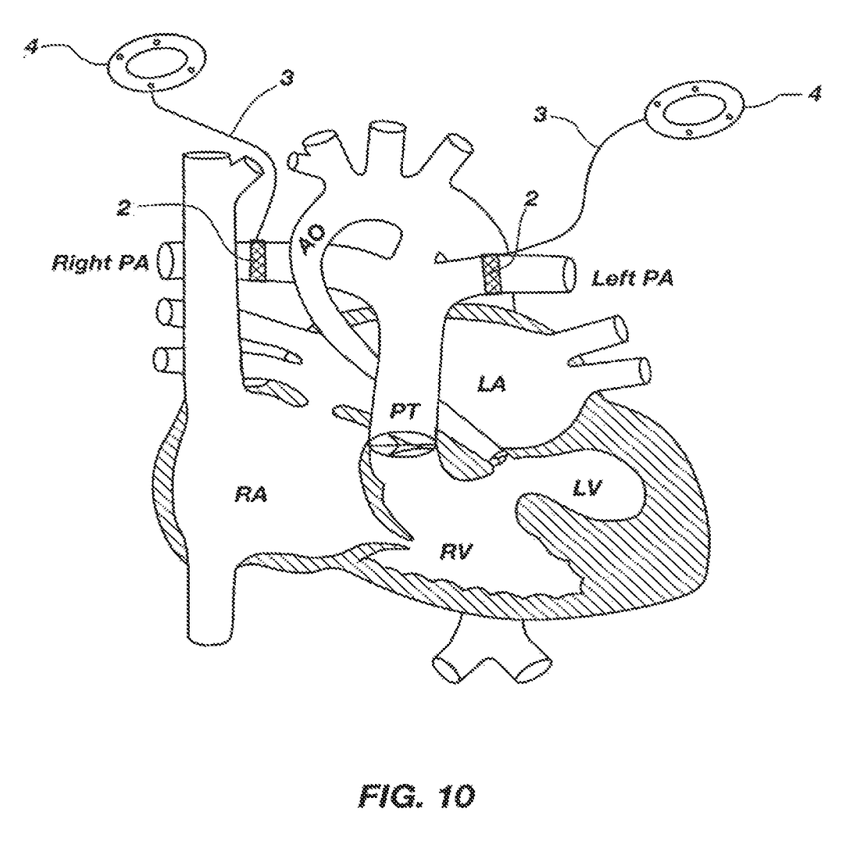
FIG. 10 is a sectional view of a heart illustrating the implantation of the banding system of FIG. 7 in the HLHS.
Figure 11:
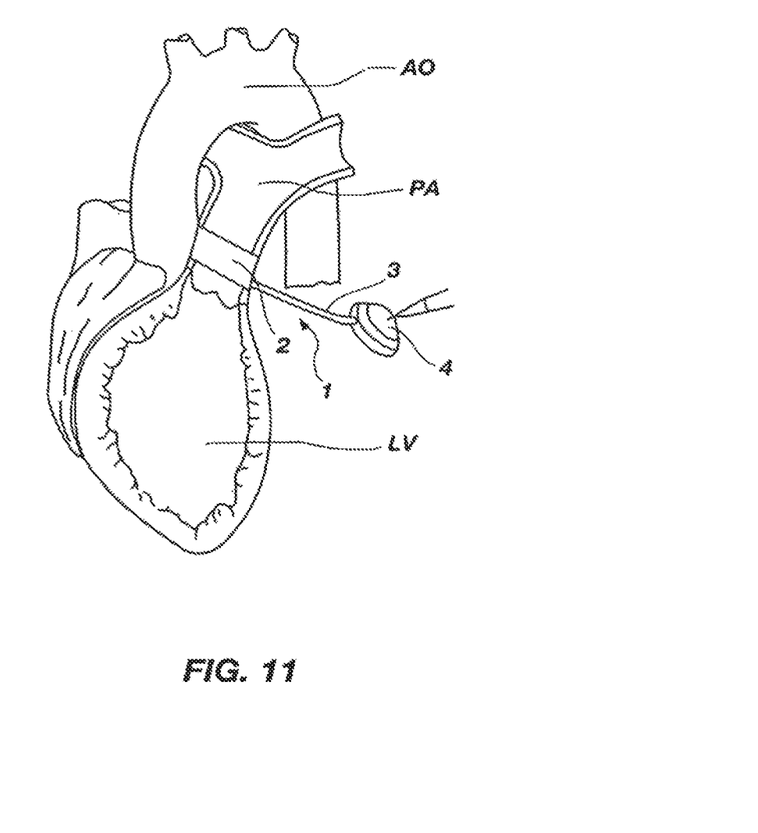
FIG. 11 is a sectional view of a hear illustrating the implantation of the banding system of FIG. 7 in the Left Ventricle for retraining.

Thus, in the surgery, once the banding ring (2) of the improved device (1) implanted in the patient pulmonary artery (PA), and once housed the insufflating button (4) in the subcutaneous thoracic wall, as shown in FIG. 6, the insufflating button is tested by an insulin needle puncture, being aspired of all the air of the system.

Then an appropriate liquid is insufflated through a needle to inside insufflating button (4), which, can be made in auto-stamped material to prevent leaking. That liquid is transmitted through the extending tube (3) until the banding ring (2) already fastened around the pulmonary artery, and already it's insufflated.

The banding ring (2) is forced to insufflate radial inside (centripetal distention), causing the pulmonary artery compression (PA), and consequently, the internal caliber reduction.

Through echocardiogram and pulse oximetrics, it is verified if the pressure disposed by the banding ring (2) over the pulmonary artery (PA) is the ideal for the moment. Through the injection of other liquid or the liquid already injected evacuated, insufflated or "uninsufflated," the banding ring (2), thus, being determined, the desired pulmonary artery pressure.

Once the implants device surgery is completed, the patient goes by the normal postoperative procedures, staying under the specific medical care for each cardiopathy that is being treated.

With the improved banding device, the perfect banding pulmonary artery adjustment is obtained, as well as the gradative squeeze pressure adjustment applied on the pulmonary artery, without any demand for new surgeries.

FIGS. 7-11 illustrate an alternative embodiment of the invention wherein similar elements to those described with reference to the first embodiment are identified with like element reference numbers.

What is claimed is:

1. A method of using an adjustable banding device for treating a patient that is an infant or neonate, comprising the steps of:
providing the adjustable banding device comprising:
an insufflating button;
said insufflation insufflating button displaying a plurality of equidistant securing holes about its outlying border;
an extending tube connected to said insufflating button and adapted to extend radially from said insufflating button to an internally inflatable banding ring, and said inflatable banding ring consisting of a thin, rigid external wall and flexible internal wall connected to said extending tube;
said inflatable banding ring configured as a hydraulic sleeve, wherein said inflatable banding ring is configured of a size and shape for at least partially encircling a blood vessel of the infant or neonate, said hydraulic sleeve including:
said external wall which is incapable of centrifugal distension;
said external wall having an upper border and a lower border;
said external wall having a first end and a second end and a first brim and a second brim extending therefrom;
wherein said first brim is a prolongation of said first end of said external wall extending away from said banding ring and configured to receive the second brim;
wherein said second brim is a prolongation of said second end of the external wall extending away from said banding ring and configured to receive the first brim;
said first and second brims capable of adjustment by accepting sutures along their lengths;
said internal wall including a thin flexible layer, such that said flexible layer of said hydraulic sleeve is capable of fine adjustment through centripetal distension radially inwardly from said external wall to at least partially compress the blood vessel upon reception of a fluid from said insufflating button and extending tube, and wherein said inflatable banding ring is configured to withstand the systemic arterial pressure of the blood vessel of the patient; and
adjusting the diameter of said external wall of said banding ring of the banding device to encircle the diameter of the blood vessel by suturing said first brim to said second brim along their lengths prior to insufflation;
adhering and securing said banding device to the blood vessel adventitia via a plurality of loops extending radially outward from each of said external wall upper and lower borders;
wherein said plurality of loops are placed equidistant on each of said external wall upper and lower borders; and
adjusting the hydraulic sleeve of said banding device through fluid injection and internal wall insufflation.

2. The method of claim 1 including the step of adjusting the banding device into a "C" shape to encircle the diameter of the blood vessel of the infant or neonate patient by suturing said first brim to said second brim at points along their lengths to adjust the diameter of the external wall of the banding ring.

3. The method of claim 2, further comprising the step of securing the banding ring external wall of the banding device to the blood vessel by suturing the loops on said upper and lower borders of said external wall to the blood vessel adventitia.

4. The method of claim 3, further comprising the steps of: placing said insufflating button subcutaneously within the thoracic wall of the patient; suturing said securing holes in the insufflating button to the patient using sutures; and
injecting fluid in the insufflating button to inflate the hydraulic sleeve of the banding device to compress the blood vessel of the infant or neonate.

5. The method of claim 1, wherein said external wall includes a thin silicone layer and a mesh for making said silicone layer rigid and non-distensible.

6. The method of claim 1, wherein said insufflating button is comprised of: a cylindrical self-sealing reservoir including silicone for receiving an injected material for adjusting said banding device, and a base including a porcelain plate for preventing a needle point from exiting said base.

7. The method of claim 6, wherein said self-sealing reservoir includes: a selfsealing silicone diaphragm at a top, a lateral aperture connected hermetically to the extending tube, and an about 3 mm thick silicone base having the securing holes around a rim to enable suturing to subcutaneous tissue, wherein the constricting of the blood vessel is adjustable by injecting or removing fluid percutaneously from the reservoir.

8. The method of claim 1, wherein said banding device is coated with medical grade silicone and includes radiopaque material.

9. A method of using an adjustable banding device for treating an infant or neonate patient, comprising the steps of:
providing the adjustable banding device comprising:
an insufflating button;
said insufflating button displaying securing holes about an outlying border;
an extending tube connected to said insufflating button and adapted to extend radially from said insufflating button to an inflating banding ring, and said inflating banding ring pre-formed into a "C" shaped cuff and connected to said extending tube via said insufflating button;
said inflating banding ring configured as a hydraulic sleeve comprising a rigid external wall and flexible internal wall;
said banding ring adapted of a size and shape for at least partially encircling a blood vessel, said hydraulic sleeve including:
said external wall incapable of centrifugal distension;
said external wall having an upper border and a lower border;
said external wall having a first end and a second end and a first brim and a second brim extending therefrom, respectively;
said first and second brims are prolongations of said first and second ends of said external wall, respectively, extending away from said "C" shaped cuff;
a plurality of loops extending radially outward from each of said upper and lower borders of said external wall for fixing the hydraulic sleeve to the blood vessel adventitia using sutures; wherein said plurality of loops are placed equidistant on each of said external wall upper and lower borders;
said first brim and said second brim configured to facilitate size banding adjustment of the banding device to a caliber of the blood vessel via placement of sutures along their lengths;
said internal wall including a thin flexible layer, wherein during compression adjustment of said banding device, said external wall is configured to constrain outward expansion of said hydraulic sleeve while said thin flexible layer is radially distended inwardly from
said hydraulic sleeve for constricting at least a portion of said blood vessel, and wherein
said inflating banding ring is configured to withstand the pressure of the blood vessel;
adjusting the banding ring diameter to encircle the outer diameter of the blood vessel of the infant or neonate patient by suturing said first brim to said second brim along their lengths;
securing the upper and lower borders of said external wall to the blood vessel by suturing said loops to the adventitia of the blood vessel;
placing said insufflating button subcutaneously within the thoracic wall of the infant or neonate patient; and
injecting fluid in the insufflating button to inflate the hydraulic sleeve of the banding device to compress the blood vessel of the infant or neonate patient.

10. The method of claim 9, wherein said external wall includes a thin silicone layer and a mesh for making said silicone layer rigid and non-distensible.

11. The method of claim 9, wherein said insufflating button is comprised of: a cylindrical self-sealing reservoir including silicone for receiving an injected material for adjusting said banding device, and a base including a porcelain plate for preventing a needle point from exiting said base.

12. The method of claim 11, wherein said insufflating button is provided with the securing holes, equally spaced apart in said base disposed close to the outlying border for providing fixation points to fix said button to the patient's thoracic wall using sutures.

13. The method of claim 11, wherein said self-sealing reservoir includes: a selfsealing silicone diaphragm at a top, a lateral aperture connected hermetically to the extending tube, and an about 3 mm thick silicone base having the securing holes around a rim to enable suturing to subcutaneous tissue, wherein the constricting of the blood vessel is adjustable by injecting or removing fluid percutaneously from the inflation reservoir.

14. The method of claim 9, wherein said banding device is coated with medical grade silicone and includes radiopaque material.

15. A method of using an adjustable banding device for treating the blood flow and pressure within a blood vessel, comprising the steps of:
providing the adjustable banding device comprising:
an insufflating button including:
a base having a plurality of holes disposed close to an outlying border of the base for providing fixation points to fix said insufflating button to a patient using sutures,
a cylindrical self-sealing reservoir attached to said base for receiving an injected material for adjusting said banding device,
an extending tube connected to said self-sealing reservoir;
said insufflating button for receiving said injected material and adapted to extend radially from said base, and
an inflating banding ring configured of a size and shape for the diameter of a pulmonary artery of the patient and connected to said extending tube for receiving said injection material, said inflating banding ring including:
- a non-distensible external wall comprising a "C" shaped cuff;
- said external wall having a first end, a second end, an upper border, and a lower border;
- a first brim and a second brim which are prolongations of the first and second end of the external wall, respectively;
- a plurality of loops extending radially outward from each of said external wall upper and lower borders;
- wherein said plurality of loops are placed equidistant on each of said external wall upper and lower borders;
- wherein said first and second brims are configured for facilitating size banding adjustment of said banding device to a caliber of the pulmonary artery of the patient through selection of passage points on said first and second brims for receiving sutures;

an internal wall including a thin flexible layer for receiving the injection material for expanding said thin flexible layer for distending said internal wall inwardly away from said external wall for adjusting constriction of at least a portion of the blood vessel while said external wall constrains said thin flexible layer from distending outwardly; wherein wherein said inflating banding ring is configured as a hydraulic sleeve adapted for at least partially encircling the pulmonary artery of the patient;

wherein said inflating banding ring is configured to withstand blood flow and pressure of the patient;

adjusting the banding ring of the banding device into a "C" shape to at least partially encircle a diameter of the pulmonary artery by suturing said first brim to said second brim;

securing the banding ring to the pulmonary artery of the patient by suturing said plurality of loops to the blood vessel adventitia; and placing said insufflating button subcutaneously within the thoracic wall of the patient; securing the holes of said insufflating button to the patient using sutures; and injecting fluid in the insufflating button to inflate the hydraulic sleeve of the banding device to compress the pulmonary artery of the patient.

16. The method of claim 15, wherein said banding device is coated with medical grade silicone and includes radiopaque material.

17. The method of claim 15, further comprising the step of verifying the pressure within the blood vessel.

18. The method of claim 17, further comprising the step of adjusting the pressure within the blood vessel by injecting additional fluid in, or removing fluid from, the insufflating button to inflate or deflate the hydraulic sleeve of the banding device to respectively further compress, or reduce compression of, the pulmonary artery of the patient.

\* \* \* \* \*